United States Patent
Lin et al.

(10) Patent No.: US 6,177,071 B1
(45) Date of Patent: Jan. 23, 2001

(54) POLAR SOLVENT-IN-OIL EMULSIONS AND MULTIPLE EMULSIONS

(75) Inventors: Zuchen Lin; William James Schulz, Jr., both of Midland; Janet Mary Smith, Bay City, all of MI (US)

(73) Assignee: Dow Corning Corporation, Midland, MI (US)

( * ) Notice: Under 35 U.S.C. 154(b), the term of this patent shall be extended for 0 days.

(21) Appl. No.: 09/498,714

(22) Filed: Feb. 7, 2000

Related U.S. Application Data

(62) Division of application No. 09/435,561, filed on Nov. 8, 1999, now Pat. No. 6,080,394.

(51) Int. Cl.[7] .............................. A61K 31/74; C08K 5/24
(52) U.S. Cl. ...................... 424/78.03; 524/261; 524/379; 524/386; 524/387; 524/588
(58) Field of Search .................... 424/78.03; 524/261, 524/379, 386, 387, 588

(56) References Cited

U.S. PATENT DOCUMENTS 5,811,487 * 9/1998 Lin ........................................ 524/862
5,889,108 * 3/1999 Zhang ................................... 524/862
5,948,855 * 9/1999 Lin ........................................ 524/839

* cited by examiner

*Primary Examiner*—Morton Foelak
(74) *Attorney, Agent, or Firm*—James L. De Cesare

(57) ABSTRACT

One composition is a non-aqueous polar solvent-in-oil emulsion containing a non-aqueous polar solvent phase dispersed in a silicone oil continuous phase by an emulsifier. A second composition is a non-aqueous polar solvent-in-oil-in-water multiple emulsion of the type $PS_1/O/W$ which contains a non-aqueous polar solvent phase $PS_1$ dispersed in a silicone oil as a first continuous phase of a primary emulsion $PS_1/O$ by an emulsifier. The primary emulsion $PS_1/O$ is dispersed in a second continuous aqueous phase W to form multiple emulsion $PS_1/O/W$. A third composition is a non-aqueous polar solvent-in-oil-in-non-aqueous polar solvent multiple emulsion of the type $PS_1/O/PS_2$ which contains a non-aqueous polar solvent phase $PS_1$ dispersed in a silicone oil as a first continuous phase of a primary emulsion $PS_1/O$ by an emulsifier. The primary emulsion $PS_1/O$ is dispersed in a second continuous non-aqueous polar solvent phase $PS_2$ to form multiple emulsion $PS_1/O/PS_2$.

6 Claims, No Drawings

POLAR SOLVENT-IN-OIL EMULSIONS AND MULTIPLE EMULSIONS

CROSS-REFERENCE TO RELATED APPLICATIONS

This application is a division of prior copending application U.S. Ser. No. 09/435,561, filed on Nov. 8, 1999 U.S. Pat. No. 6,080,394.

STATEMENT REGARDING FEDERALLY SPONSORED RESEARCH OR DEVELOPMENT

Not applicable.

REFERENCE TO A MICROFICHE APPENDIX

Not applicable.

FIELD OF THE INVENTION

This invention is directed to (i) polar solvent-in-oil emulsions $PS_1/O$, (ii) polar solvent-in-oil-in-water multiple emulsions $PS_1/O/W$, and (iii) polar solvent-in-oil-in-polar solvent multiple emulsions $PS_1/O/PS_2$. In particular, these emulsions contain a non-aqueous polar solvent(s).

BACKGROUND OF THE INVENTION

U.S. Pat. No. 5,948,855 (Sept. 7, 1999) describes certain water-in-oil emulsions $W_1/O$ and multiple emulsions $W_1/O/W_2$ which can be prepared with crosslinked elastomeric silicone polyethers as an emulsifier. These crosslinked elastomeric silicone polyethers and methods for their preparation are described in U.S. Pat. No. 5,811,487 (Sept. 22, 1998) and in U.S. Pat. No. 5,889,108 (Mar. 30, 1999). These patents are assigned to the same assignee as the present invention.

However, none of the common assignee's patents describe the use of the crosslinked elastomeric silicone polyethers as emulsifiers for preparing non-aqueous polar solvent-in-oil emulsions $PS_1/O$ and multiple emulsions $PS_1/O/W$ and $PS_1/O/PS_2$. The advantage of emulsions of the type $PS_1/O$, $PS_1/O/W$, and $PS_1/O/PS_2$, is that they can be used to deliver polar actives such as Vitamin C or activated antiperspirant salts such as aluminum chlorohydrate and aluminum-zirconium trichlorohydrate, which are known to have much better chemical stability in non-aqueous polar solvents such as propylene glycol than in water.

BRIEF SUMMARY OF THE INVENTION

In a first embodiment, the invention relates to a composition which is a non-aqueous polar solvent-in-oil emulsion containing a non-aqueous polar solvent phase dispersed in a silicone oil continuous phase by an emulsifier.

In a second embodiment, the invention relates to a composition which is a non-aqueous polar solvent-in-oil-in-water multiple emulsion of the type $PS_1/O/W$ which contains a non-aqueous polar solvent phase $PS_1$ dispersed in a silicone oil as a first continuous phase of a primary emulsion $PS_1/O$ by an emulsifier. The primary emulsion $PS_1/O$ is dispersed in a second continuous aqueous phase W to form the multiple emulsion $PS_1/O/W$.

In a third embodiment, the invention relates to a composition which is a non-aqueous polar solvent-in-oil-in-non-aqueous polar solvent multiple emulsion of the type $PS_1/O/PS_2$ which contains a non-aqueous polar solvent phase $PS_1$ dispersed in a silicone oil as a first continuous phase of a primary emulsion $PS_1/O$ by an emulsifier. The primary emulsion $PS_1/O$ is dispersed in a second continuous non-aqueous polar solvent phase $PS_2$ to form the multiple emulsion $PS_1/O/PS_2$.

In the three embodiments, the emulsifier is a crosslinked elastomeric silicone polyether constituting polymeric molecules crosslinked together to form a gel consisting of three-dimensional molecular polymeric networks containing tens, hundreds, and thousands of crosslinking units between and among the polymeric molecules. The crosslinked elastomeric silicone polyether contains and is swollen by about 65 to about 98 percent by weight of a silicone oil.

These and other features of the invention will become apparent from a consideration of the detailed description.

BRIEF DESCRIPTION OF THE SEVERAL VIEWS OF THE DRAWING

Not applicable.

DETAILED DESCRIPTION OF THE INVENTION

Emulsions are composed of droplets of one liquid dispersed in a second liquid. Multiple emulsions are composed of droplets of one liquid dispersed in a second liquid, which is then dispersed in a final continuous phase. Generally, the internal droplet phase will be miscible with or identical to the final continuous phase.

For example, in a water-in-oil-in-water multiple emulsion W/O/W, the internal phase and the external phase are both aqueous. In a non-aqueous polar solvent-in-oil-in-water multiple emulsion $PS_1/O/W$, the internal phase is a non-aqueous polar solvent and external phase is aqueous. In a non-aqueous polar solvent-in-oil-in-non-aqueous polar solvent multiple emulsion $PS_1/O/PS_2$, the internal phase and the external phase are both non-aqueous polar solvents.

For the system $PS_1/O/W$ in which the final continuous phase is aqueous, the primary emulsion is polar solvent-in-oil emulsion $PS_1/O$, which is then emulsified into the final aqueous phase W. For the system $PS_1/O/PS_2$ in which the final continuous phase is a polar solvent, the primary emulsion is polar solvent-in-oil emulsion $PS_1/O$, which is then emulsified into the final polar solvent phase $PS_2$.

For the purpose of clarity, and in accordance with recognized standards of nomenclature used for a $PS_1/O/W$ system, the oil phase of the primary emulsion is designated as O, and the primary emulsion is designated $PS_1/O$. Primary emulsion $PS_1/O$ includes polar solvent phase $PS_1$. After primary emulsion $PS_1/O$ has been further dispersed in the final aqueous phase W, this multiple emulsion is designated $PS_1/O/W$. For a $PS_1/O/PS_2$ system, the oil phase of the primary emulsion is again O, and the primary emulsion is $PS_1/O$. Primary emulsion $PS_1/O$ includes polar solvent phase $PS_1$. After primary emulsion $PS_1/O$ has been further dispersed in the final and second polar solvent phase $PS_2$, this multiple emulsion is designated as $PS_1/O/PS_2$.

Crosslinked elastomeric silicone polyethers which are used in forming these emulsions, and methods for preparing these crosslinked elastomeric silicone polyethers are described in detail in the common assignee's U.S. Pat. No. 5,811,487, incorporated herein by reference.

Generally, such crosslinked elastomeric silicone polyethers are prepared by reacting an $\equiv$Si—H containing polysiloxane (A) and a mono-alkenyl polyether (B) in the presence of a platinum catalyst, until an $\equiv$Si—H containing siloxane with polyether groups (C) is formed. The $\equiv$Si—H containing siloxane with polyether groups (C) is then reacted with an unsaturated hydrocarbon (D) such as an alpha, omega-diene, in the presence of a solvent (E) and a platinum catalyst, until a silicone elastomer is formed by crosslinking and addition of ≡SiH across double bonds in the alpha, omega-diene (D).

These crosslinked elastomeric silicone polyethers can be generally described as constituting polymeric molecules which are crosslinked together to form gels consisting of three-dimensional molecular polymeric networks containing tens, hundreds, and thousands of crosslinked units between and among the polymeric molecules. Typically, these crosslinked elastomeric silicone polyethers contain and are swollen by 65 to 98 percent by weight of an oil.

Both U.S. Pat. No. 5,811,487 and U.S. Pat. No. 5,889,108 contain extensive lists of appropriate oils which can be used, among which are, for example, (i) volatile polydimethylsiloxanes such as hexamethyldisiloxane, octamethyltrisiloxane, and decamethylcyclopentasiloxane, (ii) nonvolatile polydimethylsiloxanes having a viscosity generally in the range of about 5 to about 1,000 centistoke ($mm^2/s$), and (i) fragrances such as musk and myrrh.

Organic oils such as natural oils derived from animal, vegetable, or mineral sources, are also suitable. Modern cosmetic oils, for example, are most representative, and among common organic oils known to be safe for cosmetic purposes are almond oil, apricot kernel oil, avocado oil, cacao butter (theobroma oil), carrot seed oil, castor oil, citrus seed oil, coconut oil, corn oil, cottonseed oil, cucumber oil, egg oil, jojoba oil, lanolin oil, linseed oil, mineral oil, mink oil, olive oil, palm kernel oil, peach kernel oil, peanut oil, rapeseed oil, safflower oil, sesame oil, shark liver oil, soybean oil, sunflower seed oil, sweet almond oil, tallow (beef) oil, tallow (mutton) oil, turtle oil, vegetable oil, whale oil, and wheat germ oil.

While the term non-aqueous polar solvent is intended to include solvents generally, when the emulsions and multiple emulsions are intended for personal care application, then the non-aqueous polar solvent should be one recognized as being cosmetically acceptable. Representative of some cosmetically acceptable non-aqueous polar solvents which can be used are, for example, monohydroxy alcohols such as ethyl alcohol and isopropyl alcohol; diols and triols such as propylene glycol and glycerol, respectively; glycerol esters such as glyceryl triacetate (triacetin), glyceryl tripropionate (tripropionin), and glyceryl tributyrate (tributyrin); and polyglycols such as polyethylene glycol. In applications other than personal care, these and other more suitable types of non-aqueous polar solvents can be employed.

In using crosslinked elastomeric silicone polyethers for preparing non-aqueous polar solvent-in-oil emulsions consisting of a non-aqueous polar solvent disperse phase and an oil continuous phase, the non-aqueous polar solvent phase may contain a non-aqueous polar solvent soluble active ingredient, and the oil phase may contain an oil soluble active ingredient.

Some representative non-aqueous polar solvent soluble active ingredients for the non-aqueous polar solvent phase of the non-aqueous polar solvent-in-oil emulsion and multiple emulsion are (i) non-aqueous polar solvent soluble Vitamins, (ii) non-aqueous polar solvent soluble drugs including activated antiperspirant salts such as aluminum chlorohydrate and aluminum-zirconium trichlorohydrate, or (iii) α-hydroxy acids such as glycolic acid, lactic acid, tartaric acid, and citric acid, i.e., fruit acids. In this latter instance, i.e., (iii), significant benefits can be realized as fruit acids have been alleged to be capable of diminishing fine skin lines and pigmentation spots, as well as stimulating collagen which allows the skin to repair itself.

The common assignee's U.S. Pat. No. 5,948,855 contains an extensive list of some appropriate non-aqueous polar solvent soluble Vitamins and non-aqueous polar solvent soluble drugs which can be used, among which are Vitamin C, Vitamin $B_1$, Vitamin $B_2$, Vitamin $B_6$, Vitamin $B_{12}$, niacin, folic acid, biotin, and pantothenic acid. The non-aqueous polar solvent soluble vitamin can be used in the non-aqueous polar solvent-in-oil emulsions and multiple emulsions in amounts of from 0.01 to about 50 percent by weight.

The common assignee's U.S. Pat. No. 5,948,855 also contains an extensive list of some appropriate oil soluble active ingredients such as vitamins and drugs which can be used in the oil phase of the non-aqueous polar solvent-in-oil emulsions and multiple emulsions, among which are vitamins, including but not limited to, Vitamin $A_1$, RETINOL, $C_2$–$C_{18}$ esters of RETINOL, Vitamin E, TOCOPHEROL, esters of Vitamin E, and mixtures thereof. RETINOL includes trans-RETINOL, 13-cis-RETINOL, 11-cis-RETINOL, 9-cis-RETINOL, and 3,4-didehydro-RETINOL. Other vitamins which are appropriate include RETINYL ACETATE, RETINYL PALMITATE, RETINYL PROPIONATE, α-TOCOPHEROL, TOCOPHERSOLAN, TOCOPHERYL ACETATE, TOCOPHERYL LINOLEATE, TOCOPHERYL NICOTINATE, and TOCOPHERYL SUCCINATE. The oil-soluble vitamin or drug can be used in the non-aqueous polar solvent-in-oil emulsions and multiple emulsions in amounts of from 0.01 to about 50 percent by weight.

In forming the primary emulsion $PS_1/O$, it is preferred to use 0.1 to 99 percent by weight of the non-aqueous polar solvent phase $PS_1$, which amount includes the weight of the non-aqueous polar solvent and any non-aqueous polar solvent soluble active ingredient such as a vitamin(s) which may be carried therein. The oil phase O of the primary emulsion $PS_1/O$ is used in an amount of about 1 to 99.9 percent by weight, which amount includes the weight of the elastomeric silicone polyether, the oil, and the oil soluble vitamin(s) or oil soluble active ingredient included therein.

Preferably, the non-aqueous polar solvent phase including the weight of the non-aqueous polar solvent and any non-aqueous polar solvent soluble active ingredient comprises 20 to 95 percent by weight of primary emulsion $PS_1/O$, while the oil phase including the weight of the elastomeric silicone polyether, the oil, and the oil soluble vitamin(s) or oil soluble active ingredient comprises 15 to 80 percent by weight of primary emulsion $PS_1/O$.

Multiple emulsions $PS_1/O/W$ can then be prepared by simply mixing together about 0.1 to 70 percent by weight of the primary emulsion $PS_1/O$, with about 30 to 99.9 percent by weight of the final continuous phase W, which latter amount includes the weight of any water soluble active ingredient(s) contained in final continuous phase W. Generally, any active ingredient referred to above as being an appropriate active ingredient for addition to the non-aqueous polar solvent phase is also an appropriate active ingredient for addition to the final continuous phase W. Multiple emulsions of the type $PS_1/O/PS_2$ are prepared in a similar manner.

EXAMPLES

The following examples are set forth in order to illustrate this invention in more detail.

Example 1

Propylene Glycol-in-Oil Emulsion $PS_1/O$ 50.14 gram of a crosslinked elastomeric silicone polyether in decamethylcyclopentasiloxane (DS) prepared according to methods described in U.S. Pat. No. 5,811,487, in which about 9 percent of the repeating units in its backbone contained units that included the moiety —$(CH_2CH_2O)_n$— in which n had a value of 12, were weighed into a glass beaker and mixed with a mechanical mixer at 600 rpm (63 rad/s). 80.23 gram of propylene glycol were added to the glass beaker over a period of about 15 minutes using a pipette while mixing the contents of the glass beaker at 600 rpm (rad/s). The resulting propylene glycol-in-$D_5$ emulsion was a smooth white cream.

Example 2

Propylene Glycol/Oil/Water Multiple Emulsion $PS_1/O/W$

In this example, two coexisting emulsions were prepared as a final product material. One of the emulsions can be designated O'/W while the other emulsion can be designated as the $PS_1/O/W$ multiple emulsion of the present invention.

Part A. Preparation of the oil phase (O'). 10 gram of stearic acid, a product of Witco Corporation, New York, N.Y., sold under the tradename HYSTRENE FG, were weighed into a glass beaker, along with 10 gram of glycerol monostearate and polyoxyethylene stearate, a nonionic surfactant sold under the tradename ARLACEL 165 by ICI Surfactants, Wilmington, Del., and 25 gram of petrolatum, a semisolid petroleum jelly used as an emollient, and sold under the tradename WHITE PROTOPET by Witco Corporation, New York, N.Y. The purpose of stearic acid in this example was to act as an anionic surfactant, in addition to the nonionic surfactant ARLACEL 165, in order to emulsify the petroleum jelly in the O'/W emulsion. As these components are solid, they were placed in a hot water bath at 80° C. in order to melt.

Part B. Preparation of the water phase (W). 50 gram of a one percent by weight aqueous dispersion of carbomer thickener was weighed into another beaker along with 308.5 gram of hot deionized water. This dispersion was placed in a hot water bath and mixed with a mechanical mixer at 200 rpm (21 rad/s). Carbomer is a crosslinked polyacrylic acid polymer sold under the tradename CARBOPOL EDT 2001, by B. F. Goodrich Company, Brecksville, Ohio.

Part C. Neutralizer. 5.0 gram of triethanolamine were added to a glass beaker containing 50 gram of deionized water and mixed by hand using a glass stirring rod until the contents of the beaker were uniform. The purpose of triethanolamine in this example was to function as a neutralizing agent for the carbomer thickener which is slightly acidic in nature.

Part D. Preparation of primary emulsion ($PS_1/O$). 52 gram of a crosslinked elastomeric silicone polyether in $D_5$ prepared according to methods described in U.S. Pat. No. 5,811,487, in which about 20 percent of the repeating units in its backbone contained units that included the moiety —$(CH_2CH_2O)_n$— in which n had a value of 12, were weighed into a glass beaker and mixed at 600 rpm (63 rad/s) using a mechanical mixer. Over a period of about 15 minutes, 48.18 gram of propylene glycol were added to the glass beaker with a pipette and mixed. The resulting material, i.e., primary emulsion $PS_1/O$, was a white emulsion.

In this example, the elastomeric silicone polyether functions as an emulsifier for $D_5$ for forming primary emulsion $PS_1/O$. The phase O in primary emulsion $PS_1/O$ is constituted by the combination of $D_5$ and the elastomeric silicone polyether. Propylene glycol constitutes phase $PS_1$ of primary emulsion $PS_1/O$.

Preparation of multiple emulsion ($PS_1/O/W$). When Part A had been uniformly melted, the emulsion O'/W was prepared by pouring Part A into Part B, and mixing Parts A and B at 200 rpm (21 rad/s) for 5 minutes. The emulsion O'/W was then neutralized with Part C (W), and mixed for about five additional minutes. During neutralization, the speed of the mixer was gradually increased from 200 to 350 rpm (21–37 rad/s) to insure adequate mixing. The sample was removed from the hot water bath and allowed to cool to 55° C. while mixing at 350 rpm (37 rad/s). When the temperature of the sample had reached 55° C., 25 gram of Part D was added. Mixing was continued, and the sample was allowed to cool to 50° C. After cooling, 1.5 gram of DMDM hydantoin and some additional deionized water lost due to evaporation were added to the sample, and it was mixed for 5 additional minutes. DMDM hydantoin, i.e., 1,3-dimethylol-5,5-dimethyl, is a preservative most generally used for emulsions. It is sold under the trademark GLYDANT® by Lonza Incorporated, Fair Lawn, N.J.

The propylene glycol/oil/water multiple emulsion resulting from this example was a stable smooth white creamy lotion. The mean size of particles in the multiple emulsion $PS_1/O/W$ was about 3.7 μm.

While emulsions and multiple emulsions according to the present invention are useful in any application which can benefit from the attributes of an organosilicon material, they are primarily intended for use in personal care. Thus, they can be used alone or combined with cosmetic ingredients to form a number of over-the-counter (OTC) personal care products. For example, they are useful as carriers in antiperspirants and deodorants. They are lubricious and can improve the properties of skin creams, skin care lotions, moisturizers, facial treatments such as acne or wrinkle removers, personal and facial cleansers, bath oils, perfumes, colognes, sachets, sunscreens, pre-shave and after-shave lotions, liquid soaps, shaving soaps, and shaving lathers. They can be used in hair shampoos, hair conditioners, hair sprays, mousses, permanents, depilatories, and cuticle coats, to enhance gloss, and provide conditioning benefits.

In cosmetics, the emulsions and multiple emulsions can function as leveling and spreading agents for pigments in make-ups, color cosmetics, foundations, blushes, lipsticks, lip balms, eyeliners, mascaras, oil removers, color cosmetic removers, and powders. When incorporated into sticks, gels, lotions, aerosols, and roll-ons, the emulsions and multiple emulsions can impart a dry and silky-smooth feel.

The emulsions and multiple emulsions are also capable of functioning as carriers for pharmaceuticals, biocides, herbicides, pesticides, and other biologically active substances; and they have utility as additives for cellulosic or synthetic nonwoven carrier substrates used in wet-like cleansing wipes such as wet-wipes, tissues, and towels, marketed generally for personal hygiene and household cleaning tasks.

Although crosslinked elastomeric silicone polyethers prepared according to the common assignee's U.S. Pat. No. 5,811,487, are most preferred for use according to this invention, other types of crosslinked elastomeric silicone polyethers may be used provided they are similar in performance and benefits to preferred crosslinked elastomeric silicone polyethers. For example, elastomers can be prepared by using other types of organosilicon monomers as described in U.S. Pat. No. 5,948,855. They can also be prepared by one pot methods as described in common assignee's U.S. Pat. No. 5,889,108.

Other variations may be made in compounds, compositions, and methods described herein without departing from the essential features of the invention. The embodiments of the invention specifically illustrated herein are exemplary only and not intended as limitations on their scope except as defined in the appended claims.

What is claimed is:

1. A composition comprising a non-aqueous polar solvent-in-oil-in-water multiple emulsion of the type $PS_1$/O/W which contains a non-aqueous polar solvent phase $PS_1$ dispersed in a silicone oil as a first continuous phase of a primary emulsion $PS_1$/O by an emulsifier, the primary emulsion $PS_1$/O being dispersed in a second continuous aqueous phase W to form the multiple emulsion $PS_1$/O/W, the emulsifier being a crosslinked elastomeric silicone polyether constituting polymeric molecules crosslinked together to form a gel consisting of three-dimensional molecular polymeric networks containing crosslinking units between and among the polymeric molecules, the crosslinked elastomeric silicone polyether further containing and being swollen by about 65 to about 98 percent by weight of the silicone oil.

2. A composition according to claim 1 in which the non-aqueous polar solvent is selected from the group consisting of monohydroxy alcohols, diols, triols, esters, and polyglycols.

3. A composition according to claim 1 in which one or both of the non-aqueous polar solvent phase contains a non-aqueous polar solvent soluble active ingredient, or the first continuous phase contains an oil soluble active ingredient.

4. A composition according to claim 3 in which the non-aqueous polar solvent soluble active ingredient in the non-aqueous polar solvent phase is selected from the group consisting of polar solvent soluble Vitamins, polar solvent soluble drugs, activated antiperspirant salts, and α-hydroxy acids; and the oil soluble active ingredient in the first continuous phase is selected from the group consisting of volatile polydimethylsiloxanes, nonvolatile polydimethylsiloxanes, fragrances, oil soluble Vitamins, oil soluble drugs, and natural oils derived from animal, vegetable, and mineral sources.

5. A product containing the composition according to claim 1, the product being selected from the group consisting of antiperspirants, deodorants, skin creams, skin care lotions, moisturizers, acne removers, wrinkle removers, facial cleansers, bath oils, perfumes, colognes, sachets, sunscreens, pre-shave lotions, after-shave lotions, liquid soaps, shaving soaps, shaving lathers, hair shampoos, hair conditioners, hair sprays, mousses, permanents, depilatories, cuticle coats, make-up, color cosmetics, foundations, blushes, lipsticks, lip balms, eyeliners, mascara, oil removers, color cosmetic removers, pharmaceuticals, biocides, herbicides, pesticides, wet-wipes, and tissue wipes.

6. A method of treating hair, skin, or underarm comprising applying to the hair, skin, or underarm, the composition according to claim 1.

* * * * *